United States Patent [19]
McKnight et al.

[11] Patent Number: 5,880,814
[45] Date of Patent: Mar. 9, 1999

[54] VISUAL ACUITY TESTER WITH IMPROVED TEST CHARACTER GENERATION

[75] Inventors: Robert Nelson McKnight, Andover; Morey Herbert Waltuck, Sharon; John Donal Starr, Georgetown, all of Mass.; Kurt Paul Tolksdorf, Islip, N.Y.

[73] Assignee: Mentor Corporation, Santa Barbara, Calif.

[21] Appl. No.: 741,276

[22] Filed: Oct. 30, 1996

[51] Int. Cl.$^6$ .................................................. A61B 3/02
[52] U.S. Cl. ........................................ 351/239; 351/237
[58] Field of Search ................................ 351/200, 237, 351/239, 211

[56] References Cited

U.S. PATENT DOCUMENTS

| | | | |
|---|---|---|---|
| 4,239,351 | 12/1980 | Williams et al. | 351/36 |
| 4,907,282 | 3/1990 | Daly et al. | 382/9 |
| 5,026,151 | 6/1991 | Waltuck et al. | 351/246 |
| 5,121,981 | 6/1992 | Waltuck et al. | 351/243 |
| 5,337,154 | 8/1994 | Dorricott et al. | 348/448 |
| 5,589,897 | 12/1996 | Sinclair et al. | 351/239 |

OTHER PUBLICATIONS

"Basic Raster Graphics Algorithms," in *Computer Graphics Principles and Practice,* Foley, VanDam, Feiner, and Hughes (Nov., 1992).

Bach, "The Freiburg Visual Acuity Test–Automatic Measurement of Visual Acuity," in Optometry and Vision Science, Jan., 1996.

Hersch, "Digital Typography and Raster Imaging: The Desk Top of the 90's," in Eurographics Technical Report Series, Sep., 1991.

*Primary Examiner*—Huy Mai
*Attorney, Agent, or Firm*—Fish & Neave; G. Victor Treyz

[57] ABSTRACT

A visual acuity tester based on a personal computer is provided that is capable of displaying visual acuity test characters at varying sizes on a monitor. The visual acuity tester antialiases the test characters to overcome the effects of staircase distortion. Preferably, the visual acuity tester performs unweighted area sampling antialiasing. The visual acuity tester also centers the test characters relative to the pixel array of the monitor to improve the appearance of the test characters. The test characters can be centered relative to either the center of a pixel or the corner of a pixel (a pixel coordinate). Test characters can also be centered relative to a pixel center in one dimension and a pixel coordinate in the other dimension.

78 Claims, 14 Drawing Sheets

VISUAL ACUITY TESTER WITH IMPROVED TEST CHARACTER GENERATION

BACKGROUND OF THE INVENTION

This invention relates to visual acuity testing instruments, and more particularly, to visual acuity testers capable of displaying test characters with an improved appearance.

An important component of most eye examinations is a test of visual acuity, typically performed using a wall-mounted eye chart. Wall-mounted eye charts have rows of test characters of progressively decreasing size. Various test characters are commonly used, including Snellen letters, tumbling E's, tumbling C's, numbers, and other suitable patterns and test symbols. Typically, the person having his or her eyes examined (the patient) identifies as many of the test characters as possible. By determining the number of test characters of a given size that the patient is able to identify properly, the person performing the eye examination (the physician) is able to assess the patient's level of visual acuity.

Although it may be acceptable to use wall-mounted eye charts in some situations, wall-mounted eye charts are often cumbersome. Wall-mounted eye charts are designed to viewed only at a predetermined distance (known as the "lane length"). Unless the required lane length can be accommodated within the physician's office, the wall-mounted eye chart can not be used.

Physicians also examine the eyes of a variety of patients, so it is often desired to use different charts. For example, a chart made up of Snellen letters may be used to test an adult patient. When testing children, it may be preferable to use the tumbling "C" character set. Unfortunately, keeping an orderly set of wall-mounted eye charts is burdensome.

Another approach for visual acuity testing is to use a wall projector. Wall projectors are similar in design to slide projectors and allow various eye charts to be displayed on a wall for visual acuity testing. The size of the eye chart on the wall can be changed to accommodate different lane lengths by adjusting a variable magnification lens on the wall projector unit. However, making such adjustments requires careful calibration. In practice, physicians rarely change the magnification of the eye charts presented using wall projectors. In addition, providing a wide variety of charts with a wall projector can be burdensome. Because wall projectors are not capable of displaying randomly generated sets of test characters, patients sometimes memorize the sequence of test characters on the charts.

One way in which to overcome many of the drawbacks of traditional wall-mounted eye charts and wall projectors is to use an electronic display system. For example, commonly-assigned U.S. Pat. 5,121,981 by Waltuck et al., which issued Jun. 16, 1992, describes a display system in which a physician can electronically display a number of test characters at varying magnifications. However, the display system of the '981 patent is based on custom hardware, which is relatively expensive. Further, the visual quality of the test characters on the monitor in the '981 system is sometimes degraded by the staircase pixel effect known as "aliasing."

It is therefore an object of the present invention to provide an electronic display system for visual acuity testing that is economical and that can display test characters with improved visual appearance.

SUMMARY OF THE INVENTION

This and other objects of the invention are accomplished in accordance with the invention by providing a visual acuity tester capable of displaying test characters on a computer monitor using antialiasing techniques. The visual acuity tester allows the person performing an eye examination to select an eye chart thought to be suitable for a given patient. The visual acuity tester then retrieves the information necessary to display the chart and displays the test characters that make up the chart on the monitor. The visual acuity tester preferably is based on readily available personal computer hardware, which allows the visual acuity tester to be more economical than would otherwise be possible.

The visual acuity tester is capable of displaying test characters using a combination of techniques. For example, to overcome the staircase distortion that results when small test characters are displayed on a computer monitor, the visual acuity tester performs antialiasing. Preferably, the visual acuity tester uses an antialiasing technique known as unweighted area sampling. Antialiasing the test characters improves their appearance by smoothing out the jagged edges that otherwise occur when certain test characters are displayed.

The visual acuity tester also centers the test characters relative to the pixel array of the monitor in order to improve their appearance. One way in which the visual acuity tester performs centering is to center test characters relative to the center of a pixel. Another approach used by the visual acuity tester is to center the test characters relative to the corner of a pixel (a pixel coordinate). Still another technique involves centering test characters relative to the center of a pixel in one dimension while centering them relative to a pixel coordinate in the other dimension.

Further features of the invention, its nature and various advantages will be more apparent from the accompanying drawings and the following detailed description of the preferred embodiments.

BRIEF DESCRIPTION OF THE DRAWINGS

FIG. 5 is a schematic representation of the hypothetical test character uncentered with respect to the pixel array.

FIG. 6 is a schematic representation of the hypothetical test character centered about a pixel coordinate.

FIG. 7 is a schematic representation of the hypothetical test character centered about a pixel center.

FIG. 8 is a schematic representation of the hypothetical test character horizontally centered about a pixel center and vertically centered about a pixel coordinate.

FIG. 9 is a schematic representation of an antialiased version of the uncentered hypothetical test character of FIG. 5.

FIG. 10 is a schematic representation of an antialiased version of the hypothetical test character of FIG. 6.

FIG. 11 is a schematic representation of an antialiased version of the hypothetical test character of FIG. 7.

FIG. 12 is a schematic representation of an antialiased version of the hypothetical test character of FIG. 8.

DETAILED DESCRIPTION OF THE PREFERRED EMBODIMENTS

Figure 1:
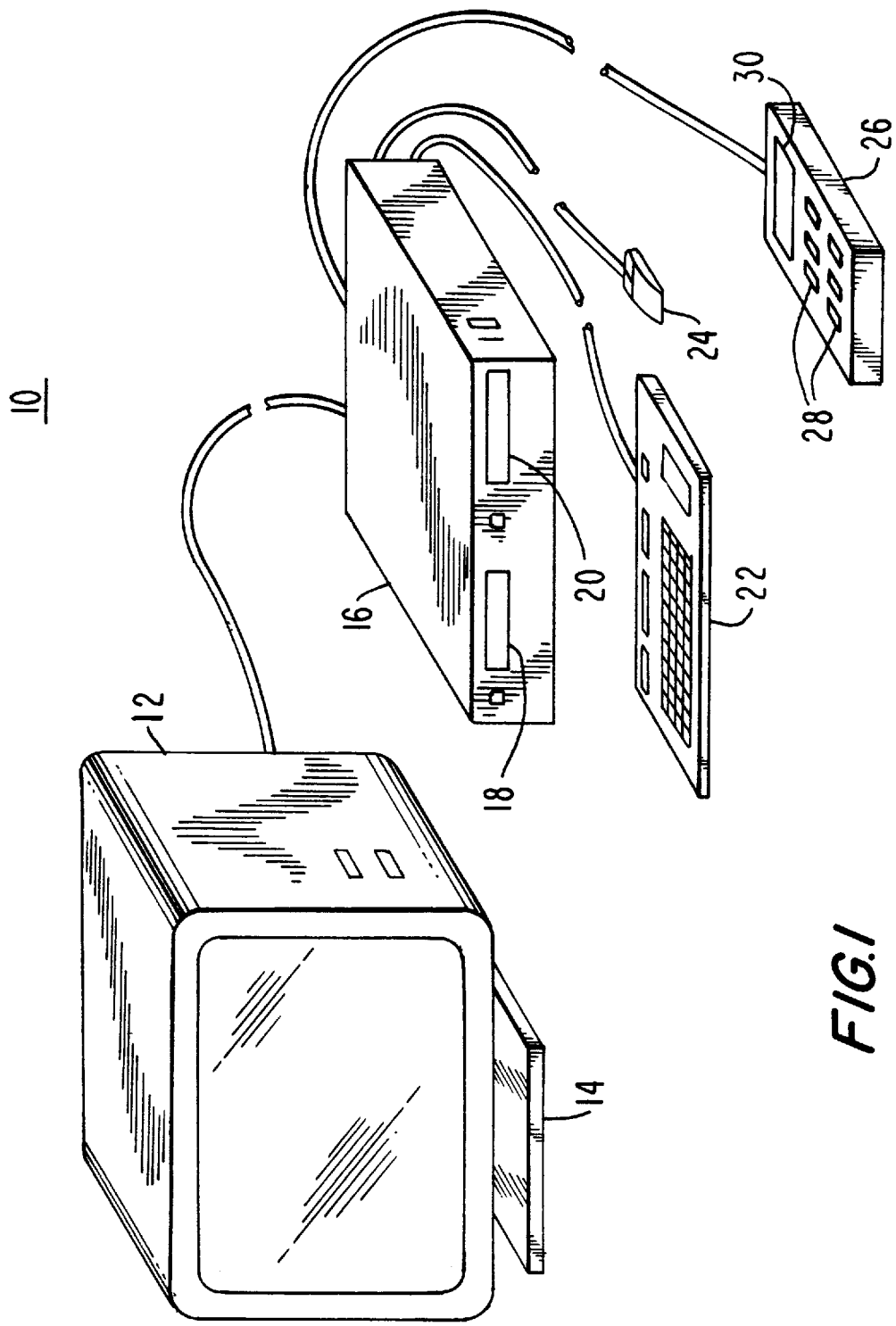
FIG. 1 is a perspective view of an illustrative visual acuity tester constructed in accordance with the present invention.

A visual acuity tester 10 constructed in accordance with the present invention is shown in FIG. 1. Visual acuity tester 10 has a monitor 12, which may be a cathode ray tube ("CRT"), plasma screen, liquid crystal display, or other suitable computer monitor. Visual acuity test characters are displayed on monitor 12, which is mounted on swivel stand 14. Preferably, monitor 12 is a 14" Video Graphics Array ("VGA") monitor having a resolution of 480×640 pixels. If desired, monitor 12 can be driven by a graphics card capable of providing 256 shades of gray (an 8-bit gray scale resolution). An economical alternative is to support 16 shades of gray (4-bit resolution).

The test characters that are displayed on monitor 12 are generated by control unit 16, which preferably is a conventional microprocessor-based personal computer. Control unit 16 preferably has sufficient computational power to display test characters of various sizes in real time. For example, control unit 16 can be based on a microprocessor such as the 80386 microprocessor available from Intel Corporation of Santa Clara, Calif. Control unit 16 may have a floppy diskette drive 18 and a compact disk read-only memory (CD-ROM) or other suitable optical disk drive 20 for receiving software updates or test character data.

Because control unit 16 is based on a conventional personal computer, control unit 16 is capable of receiving commands from a physician using conventional input interfaces, such as a trackball, pen-based computer screen, joystick, touchpad, etc. Preferably, control unit 16 receives input from a keyboard 22, a mouse 24, or from a dedicated handheld remote control unit 26.

As described in the above-mentioned U.S. Pat. 5,121,981, which is hereby incorporated by reference in its entirety, remote control unit 26 preferably has keys 28 that may be used by the physician during a patient examination to select which test characters are displayed on monitor 12. Remote control unit 26 also contains a display (preferably a liquid crystal display) that allows the physician to directly observe the characters that are currently being displayed on monitor 12.

Test characters may be displayed in a range of sizes. The smallest size of character that is typically used is 20/10. The larger character sizes—20/15, 20/20, 20/25, 20/30, 20/35, 20/40, 20/50, etc.—have heights that scale proportionally. Thus, a 20/50 character is 50/30 (1.67) times as large as a 20/30 character.

The smallest characters that average individuals with unimpaired eyesight can readily recognize are 20/20 letters. The height of a 20/20 letter subtends an angle of 5 minutes of arc. At a viewing distance of 10 feet, a 20/20 letter is 0.175 inches in height.

Rectilinear characters, such as the so-called tumbling E's, may sometimes fit perfectly within the pixel array in such a way that the characters may be accurately displayed using an integral number of pixels in both the horizontal and vertical dimensions. However, it is usually impossible to represent rectilinear test characters on the monitor accurately using an integral number of pixels. For example, on a monitor with 640×480 pixels and a pixel spacing of 13.4 mils/pixel, a 20/20 test character viewed at 10 feet is ideally 13.3 pixels in height and width. Further, even if a test character can be represented using an integral number of pixels at one size, when that character is scaled to another size, the ideal pixel height and width will usually no longer be an integral number. And other characters, such as the letter "V," have angular features that always take on a staircased appearance when small character sizes are used.

Figure 2:
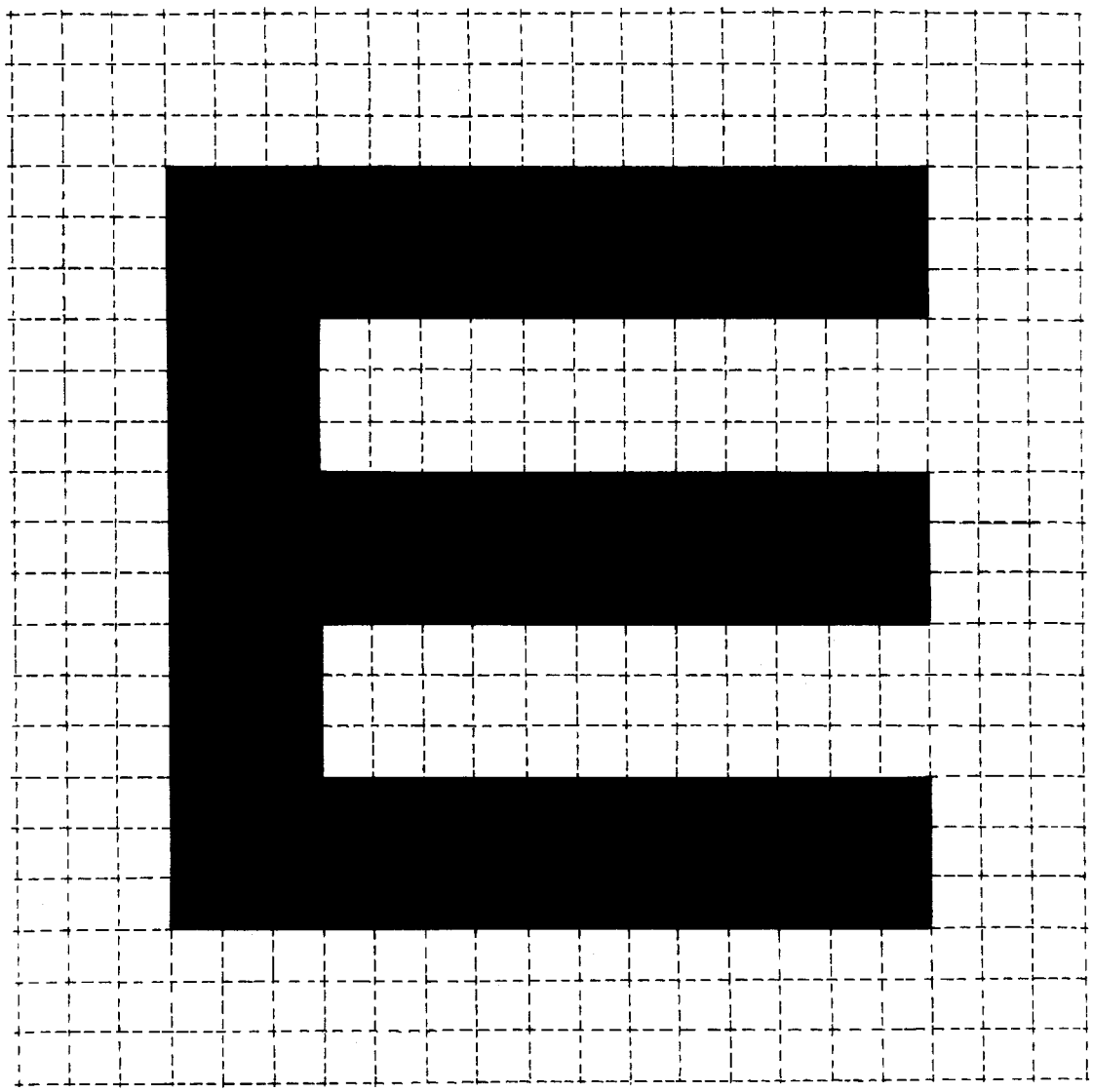
FIG. 2 is a schematic representation of a typical tumbling E as it appears using a conventional display system. The dotted lines represent the two-dimensional array of pixels on the monitor.

The staircasing effect that arises when test characters cannot be evenly accommodated within the pixel array is called aliasing. The effects of aliasing on rectilinear characters can be understood with reference to FIGS. 2 and 3. A commonly used rectilinear test character is the tumbling E. An illustrative tumbling E 32 is shown in FIG. 2. Dotted lines represent the boundaries between idealized pixels on display monitor 12 (FIG. 1). Tumbling E 32 has an ideal height of 15 pixels. Each of the three fingers of E 32 is ⅕ of the total character height, so that tumbling E 32 may be accurately represented by three horizontal rows of pixels each 3 pixels in height by 15 pixels in width.

The pixels of tumbling E 32 are black and the adjacent pixels are white, an arrangement that provides a high contrast image, but gives rise to aliasing when the E 32 has a size that does not readily fit into the pixel array.

Figure 3:
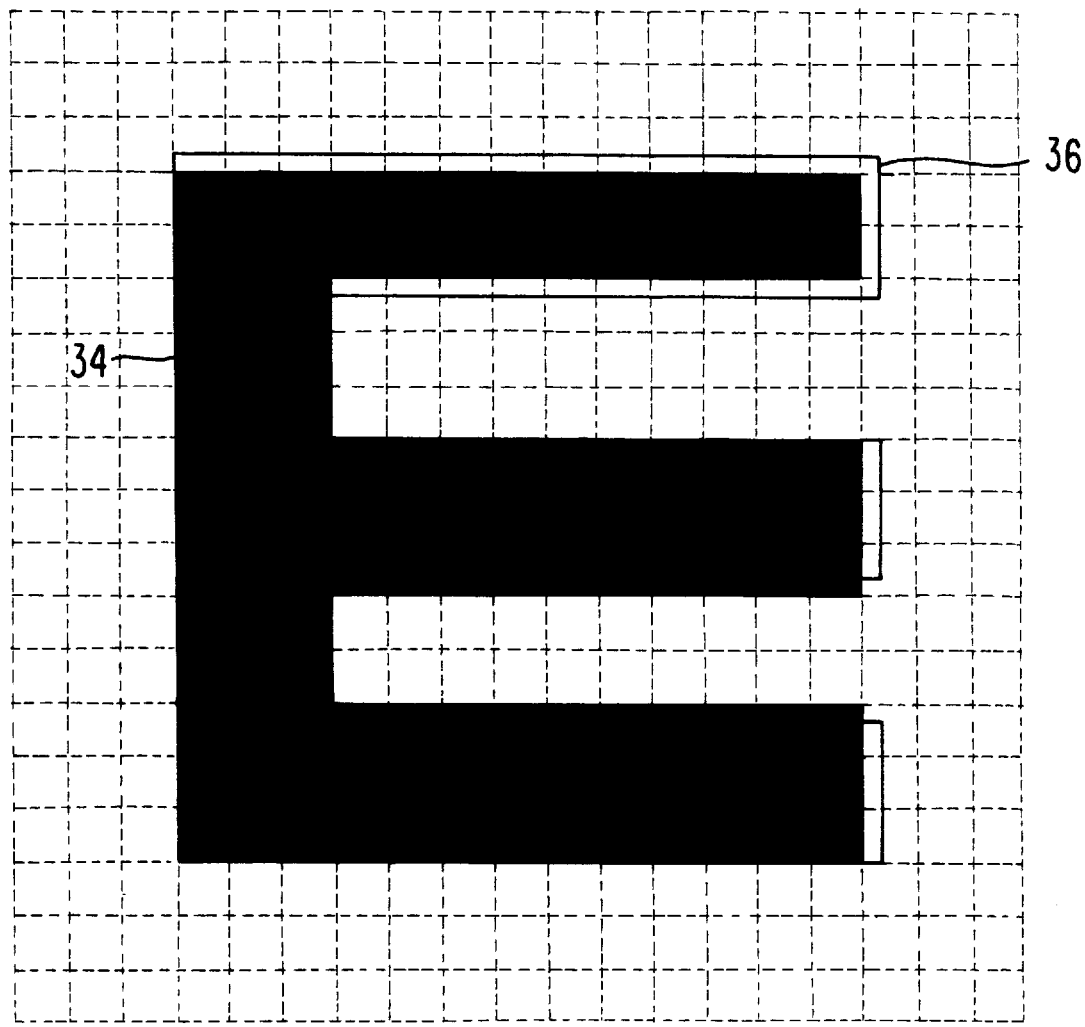
FIG. 3 is a schematic representation of the E shown in FIG. 2, scaled to a smaller size. The dotted lines represent the pixel array. The solid lines show the ideal outline of the scaled E. The darkened pixels show how the E actually appears on the monitor.

For example, if it is desired to display E 32 as a smaller test character, having non-integral pixel dimensions, then the test character will not fit evenly into the array of pixels on the display monitor and the character will appear distorted. As shown in FIG. 3, test character E 34 has an ideal height and an ideal width of 13.3 pixels (shown by outline 36). With conventional display systems, whenever the solid line 36 encompasses 50% or more of a pixel that pixel is solid black. Whenever the solid line 36 encompasses less than 50% of a pixel that pixel is white. As a result, the appearance of test characters such as E 34 is distorted, because the 13.3 pixel height and width cannot be evenly accommodated within the pixel array of the display monitor.

Thus, the lower and middle fingers of E 34 appear thicker than they should in FIG. 3. And the top finger is thinner than it would ideally be. In addition, each finger appears shorter on the display than it ideally would be if the character were scaled correctly.

Figure 4:
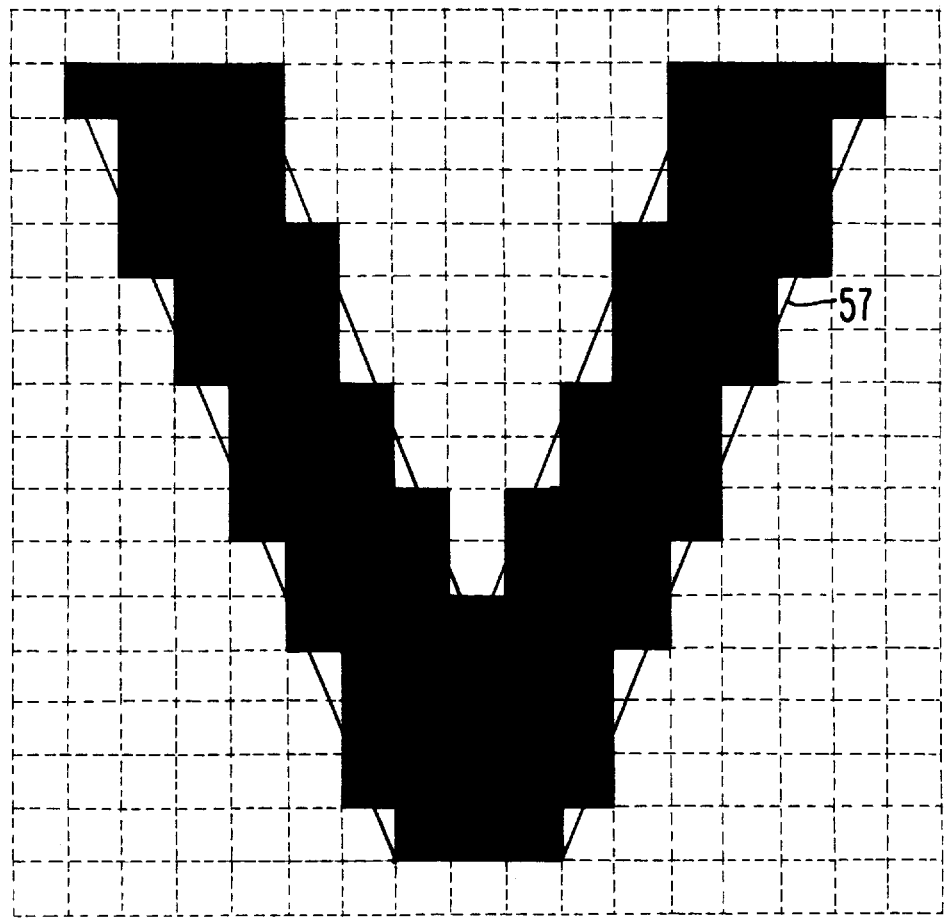
FIG. 4 is a schematic representation of a test character V as it appears using a conventional display system. The solid line is the ideal outline of the V. The darkened pixels show how the V actually appears on the monitor.

Test characters with diagonal and curved outlines are always distorted due to aliasing. For example, V 56 in FIG. 4 suffers from aliasing because the ideal shape of V 56—represented by the diagonal outline 57—cannot be evenly accommodated within the pixel array.

Another distortion commonly caused by conventional display techniques arises due to the failure to center the test character with respect to the pixel array. Thus, because E 34 of FIG. 3 is not centered, the fingers are of different sizes, which creates an asymmetrical appearance.

Although the negative impact of aliasing and failing to center the test characters can be reduced somewhat by using a display monitor with a greater pixel density, high-resolution monitors do not completely eliminate character distortions and are expensive. Therefore, in accordance with the present invention, visual acuity tester 10 (FIG. 1) uses centering and antialiasing techniques to reduce the effects of the distortion that would otherwise arise when displaying test characters at sizes that do not fit evenly in the pixel array of display monitor 12 (FIG. 1).

Visual acuity tester 10 (FIG. 1) can center the test characters relative to either the center of a pixel or to a pixel "coordinate" (the corner of a pixel). Test characters can also be centered using a combination of these two approaches. Centering the test characters makes them appear more symmetrical on monitor 12 (FIG. 1).

Visual acuity tester 10 may use any suitable technique for antialiasing the test characters. If desired, an appropriate weighted area sampling technique may be used. However, visual acuity tester 10 preferably uses a technique known as unweighted area sampling, because unweighted area sampling is less computationally intensive than weighted area sampling. Further, test characters antialiased with unweighted area sampling exhibit relatively high spatial frequencies compared with characters antialiased with weighted area sampling. Test characters with such high spatial frequencies are generally preferable for visual acuity testing.

With antialiasing, not all of the pixels that make up the test character are solid black. Rather, pixels have various shades of gray, depending on the degree of overlap between a given pixel and the ideal outline of the test character. If a pixel is entirely encompassed by the character outline, then that pixel is black. If a pixel is entirely outside of the character outline, that pixel is white. Using unweighted area sampling, the pixels that partially overlap with the ideal shape of the test character are colored gray, in direct proportion to the fractional overlap of each pixel and the ideal character shape. For example, if 20% of a pixel's area overlaps with the ideal character shape, then that pixel is illuminated at a 20% gray level. (Of course, the precise level of pixel illumination is limited by the gray scale resolution supported by the monitor and its associated video circuitry.)

The way in which visual acuity tester 10 (FIG. 1) performs antialiasing and centering is described further in connection with FIGS. 5–12. A hypothetical test character having dimensions of 1.5×1.5 pixels is shown on the left side of FIGS. 5–12 in various positions relative to the pixel grid. Also shown on the right side of FIGS. 5–12 are the pixel intensities that result using various techniques to display the hypothetical character. In FIGS. 5–12, the pixels are the squares delineated by dotted lines. The points at which the dotted lines intersect define pixel "coordinates." The pixel coordinate of each pixel is located at the lower left corner of that pixel. Each pixel also has a center, defined as the point midway (in both the horizontal and vertical directions) from its border.

Figure 5:
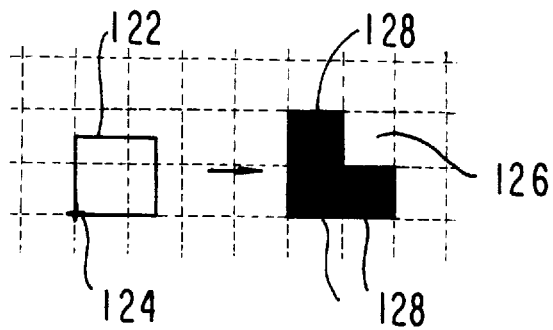
FIGS. 5–12 are schematic representations of a hypothetical test character. The ideal outline of the character in relation to the pixel array is shown on the left side of FIGS. 5–12. On the right side of FIGS. 5–12, the hypothetical test character is shown as it actually appears on the monitor.

FIG. 5 shows outline 122 of the hypothetical test character aligned with the pixel array in such a way that lower left point 124 of outline 122 is aligned with a pixel coordinate (represented by the small cross). With this arrangement, outline 122 is not centered with respect to the pixel array. The resulting appearance of the hypothetical test character displayed using conventional techniques is shown on the right side of FIG. 5. Pixel 126, which only overlaps 25% with outline 122, is white. Pixels 128, which each overlap 50% or more with outline 122, are black. The appearance of the hypothetical test character using this approach is distorted.

Figure 6:
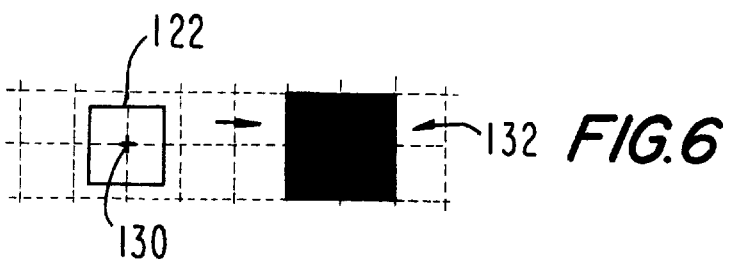

In accordance with the present invention, visual acuity tester 10 (FIG. 1) preferably centers outline 122 relative to the pixel array. As shown in FIG. 6, one way in which the test character can be centered is to align the character so that the vertical and horizontal portions of outline 122 are equidistant from a pixel coordinate. When visual acuity tester 10 uses this technique, outline 122 is centered about pixel coordinate 130 and the hypothetical test character appears as a block of four symmetrically arranged pixels 132, as shown on the right side of FIG. 6.

Figure 7:
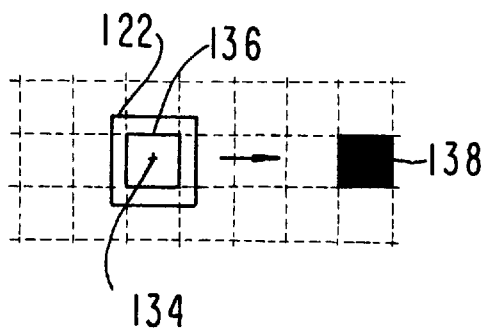

Another centering technique is to align the test character so that the vertical and horizontal portions of outline 122 are centered with respect to the center of a pixel, as shown in FIG. 7. With this approach, outline 122 is centered about pixel center 134 of pixel 136. The resulting hypothetical test character appears on the monitor as a single pixel 138.

Figure 8:
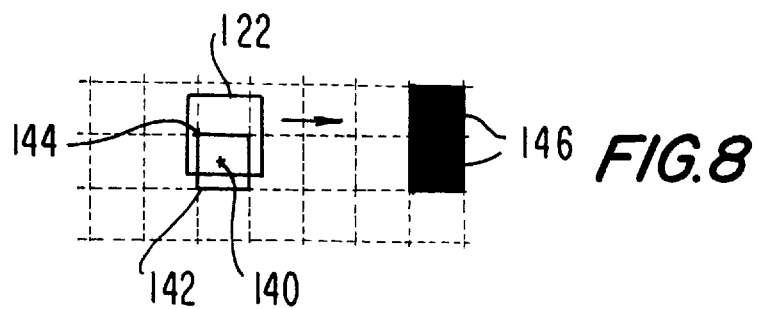

Still another centering technique involves simultaneously centering the test character in one dimension (horizontal or vertical) about a pixel coordinate, while centering in the other dimension about a pixel center. This approach is illustrated in FIG. 8. Outline 122 is centered in the horizontal dimension about pixel center 140 of pixel 142. In the vertical dimension, outline 122 is centered about pixel coordinate 144. The resulting appearance of the test character is in the form of two pixels 146, as shown on the right side of FIG. 8.

Figure 9:
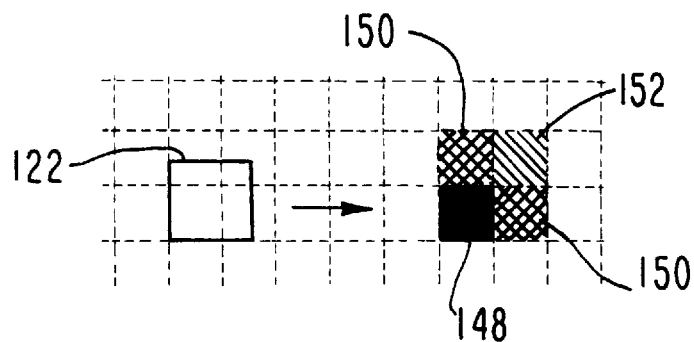
Figure 10:
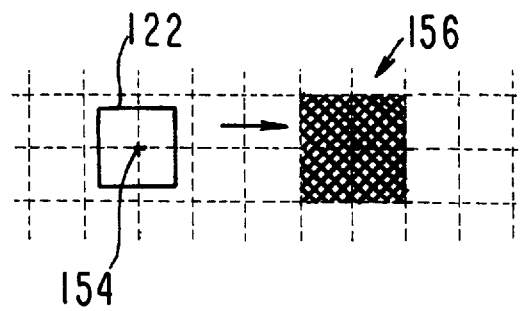

The appearance of the hypothetical test character antialiased with the unweighted area sampling technique is shown in FIGS. 9–12. As shown in FIG. 9, outline 122 of the test character overlaps four pixels. Pixel 148 falls 100% within the ideal character shape defined by outline 122. Accordingly, pixel 148 is black. Pixels 150 have a 50% overlap with the ideal shape of the hypothetical test character. Pixels 150 are therefore assigned a gray level of 50%. Pixel 152 falls 25% within the outline 122, so pixel 152 has a 25% gray level. As described in more detail below, the process of antialiasing the test characters used by visual acuity tester 10 (FIG. 1) improves the appearance of the test characters by smoothing out the jagged edges that arise due to the inability of the ideal test character shape to be accommodated within the pixel array. Although visual acuity tester 10 can improve the appearance of the test characters using either centering or antialiasing alone, preferably, both centering and antialiasing are preformed.

If the hypothetical test character is centered with respect to the pixel array as well as antialiased, the test character appears more symmetrical. For example, in FIG. 10, outline 122 is centered about pixel coordinate 154. The resulting antialiased test character is made up of a group of four pixels 156, each assigned a gray level of 56.25%, because each pixel overlaps 56.25% with the ideal shape of the hypothetical test character.

Figure 11:
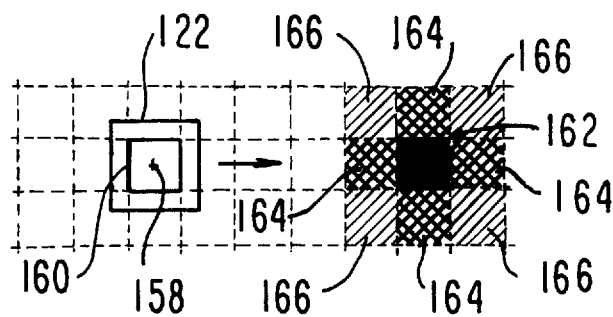
Figure 12:
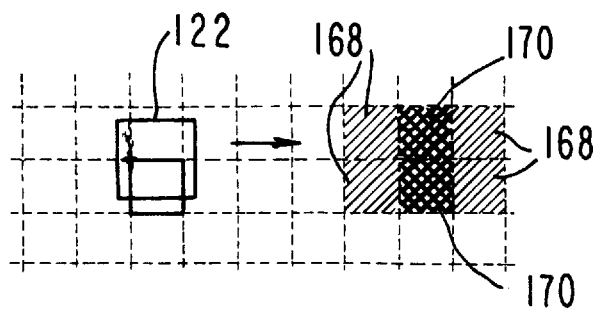

As shown in FIG. 11, if the hypothetical test character is centered with respect to pixel center 158 of pixel 160, the test character appears on monitor 12 as group of 9 pixels of varying gray levels. Central pixel 162 is black, because pixel 162 falls completely within the outline 122. Pixels 164 have a gray level of 25%, because 25% of each pixel 164 is contained within outline 122. Pixels 166 have a gray level of 6.25%, because that is the extent to which pixels 166 overlap with the shape of the hypothetical test character.

Antialiasing can also be performed if the test character is centered about a pixel coordinate in one dimension while being centered about a pixel center in the other dimension. The appearance of test character 122 following this type of Processing is shown on the right side of FIG. 12. Pixels 168 have a 18.75% gray level, because 18.75% of pixels 168 fall within outline 122 of the hypothetical test character. Pixels 170 have a 75% gray level, because 75% of pixels 170 are within outline 122.

Figure 13:
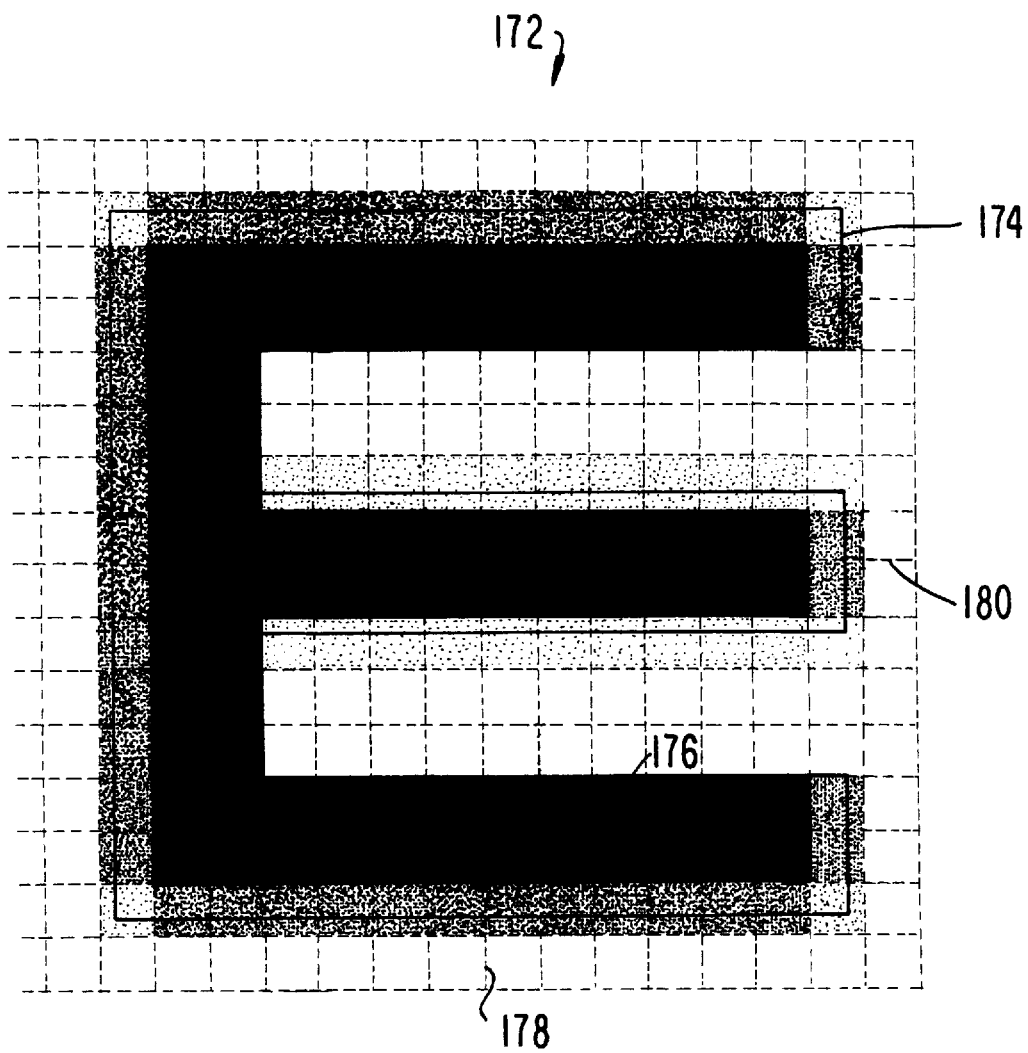
FIG. 13 is a schematic representation of an antialiased tumbling E centered about a pixel coordinate.
Figure 14:
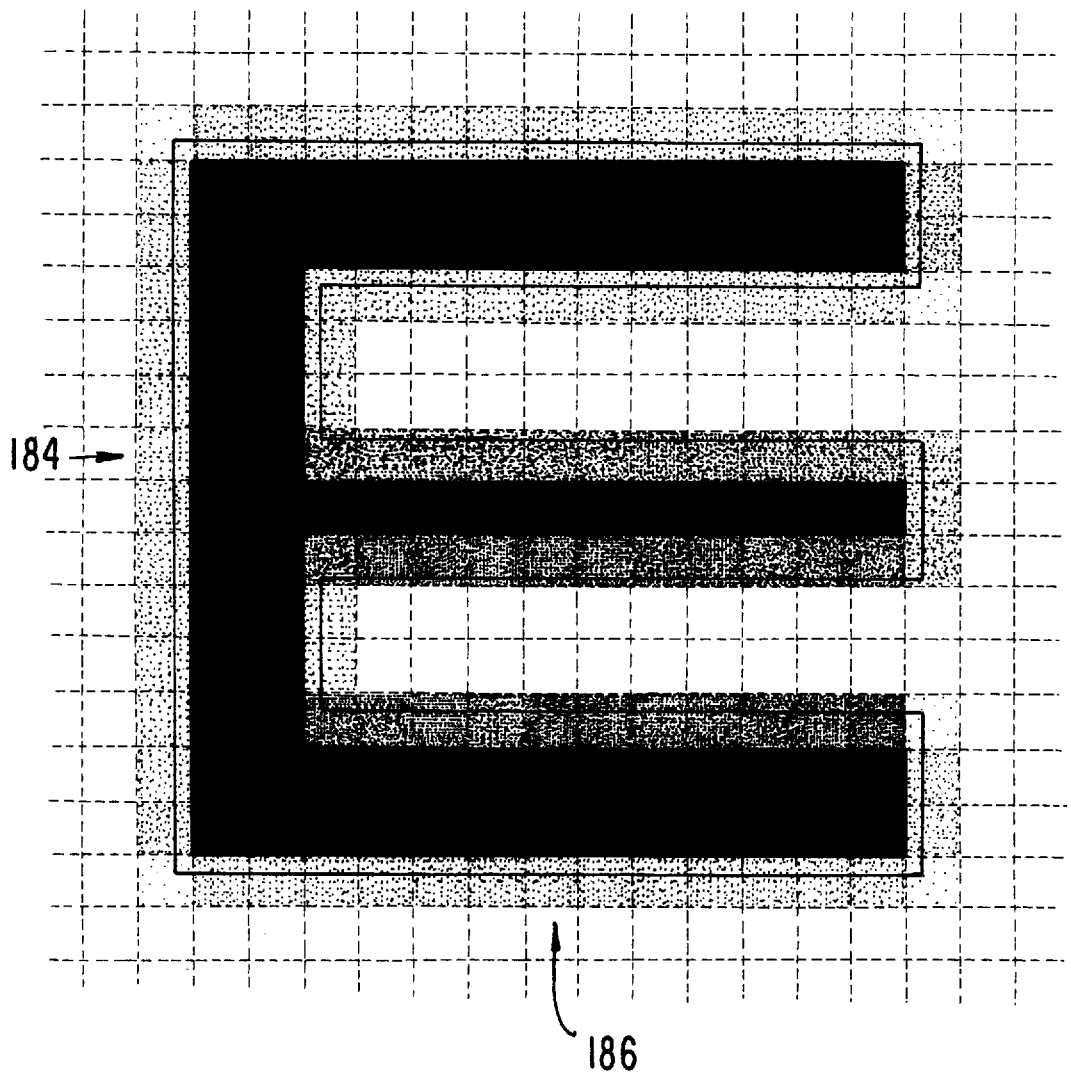
FIG. 14 is a schematic representation of an antialiased tumbling E centered about a pixel center.
Figure 15:
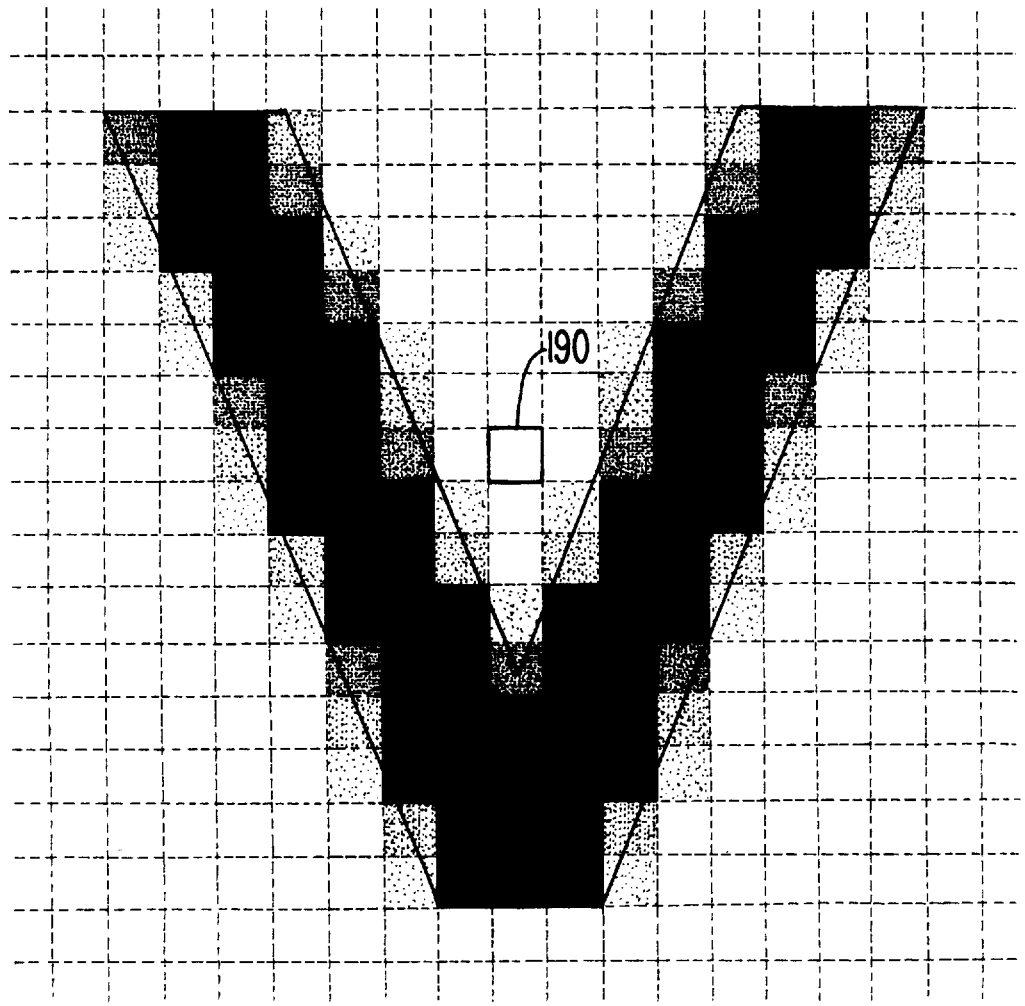
FIG. 15 is a schematic representation of an antialiased V centered about a pixel center.

The effects of antialiasing and centering the test characters such as a tumbling E and the letter V are shown in FIGS. 13–15. As shown in FIG. 13, tumbling E 172 has ideal pixel dimensions of 13.3—13.3 pixels (as was the case for the distorted tumbling E 34 of FIG. 3). The ideal shape of tumbling E 172 is given by solid outline 174. Pixels such as pixel 176, which fall entirely within outline 174 are colored black. Pixels outside of the outline 174 are white. The pixels that partially overlap with the ideal shape of E 172 preferably are shaded using the unweighted area technique described above. Tumbling E 172 is centered with respect to the pixel array. Specifically, tumbling E 172 is centered about the pixel coordinate that lies at the intersection of vertical dotted line 178 and horizontal dotted line 180. Antialiased tumbling E 182 of FIG. 14 is similar to tumbling E 172 of FIG. 13, except that tumbling E 182 is centered about the center of the pixel in row 184 and column 186, rather than being centered about a pixel coordinate. FIG. 15 shows an antialiased and centered V test character. As shown in FIG. 15, antialiased V 188 is centered about the center of pixel 190.

The way in which visual acuity tester 10 (FIG. 1) centers and antialiases tumbling E 172, tumbling E 182, and V 188 substantially improves the appearance of these test characters. When viewed from a distance, the gray pixels blend with the black pixels to create characters on display monitor 12 that are smoother and more balanced than the characters displayed on previously known visual acuity testers. As a result, the test characters displayed on monitor 12 are well suited for testing a patient's visual acuity.

The control unit is provided with a suitable set of computer instructions that allow control unit 16 (FIG. 1) to perform the various functions required by the visual acuity tester 10. Preferably, the computer instructions for controlling visual acuity tester 10 are stored on an appropriate storage device such as an internal hard disk drive (e.g., data storage device 92 in FIG. 19). When it is desired to execute the instructions, the instructions are loaded into the random-access memory 98 of control unit 16. During the initial set-up and the subsequent operation of visual acuity tester 10, control unit 16 executes the instructions.

Figure 16:
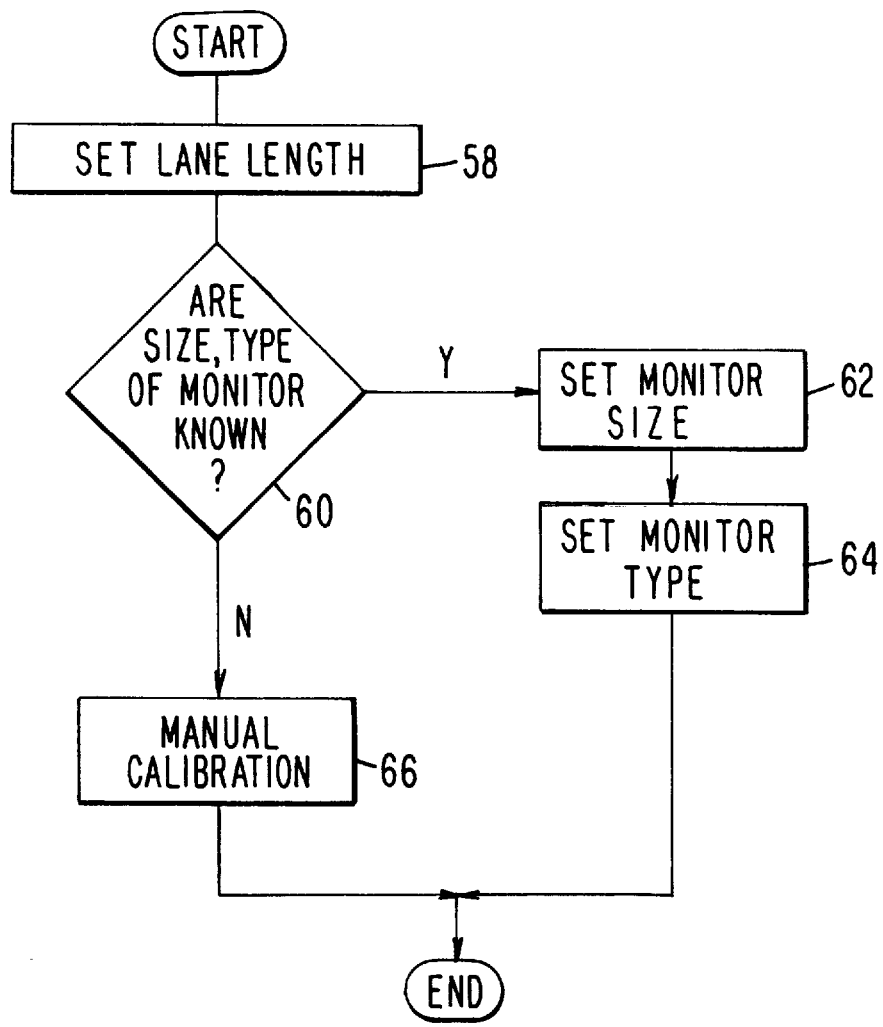
FIG. 16 is a flow chart depicting various settings of the visual acuity tester that may be adjusted during a set-up routine.

Before visual acuity tester 10 is used to evaluate a patient's vision for the first time, the physician sets up the tester. Because visual acuity tester 10 may preferably be implemented on any suitable personal computer, some variables, such as the monitor size and the lane length, will generally not be programmed into visual acuity tester 10 prior to set up. The lane length, which is the fixed distance between the patient's eyes and display 12, typically ranges from 10 to 20 feet, depending on the physical arrangement of the physician's office. As shown schematically in FIG. 16, when setting up visual acuity tester 10, the physician selects the desired lane length at step 58. At test 60 it is determined whether the type and size of monitor 12 (FIG. 1) are known. If the size or type of the monitor is known, then the physician responds accordingly at test 60. The physician may enter the monitor size (e.g., 14 inches) at step 62. Similarly, if the type of the monitor (e.g. VGA) is known, then the physician may enter this information at step 64. The physician may enter the necessary information directly using keyboard 22 (FIG. 1), remote control unit 26, or other suitable input interface. Alternatively, the physician may select a monitor model name from a list of such model names provided by visual acuity tester 10.

If the monitor type and size are not known with certainty, then at test 60 the physician can choose to perform a manual calibration. If manual calibration is desired, visual acuity tester 10 generates a suitable calibration pattern at step 66. Suitable calibration patterns include a square approximately three inches high by three inches wide or horizontal and vertical bars. The physician preferably uses a template or ruler to measure the actual size at which the calibration pattern is displayed on monitor 12 (FIG. 1). The size of the calibration pattern on the display can then be adjusted via keyboard 22, until it precisely matches the size of the template. Thus, for example, if the calibration pattern is a vertical bar and a horizontal bar, the physician can adjust the size of the vertical bar using the up and down arrow keys and the size of the horizontal bar using the left and right arrow keys. Generally, no additional set-up steps are required beyond calibrating the size of the characters on the display and selecting the lane length.

Other settings, such as those that determine which test characters are to be used when examining a patient, are typically selected during normal operation of visual acuity tester 10. Such physician-selectable settings are chosen during the steps in block 68, shown schematically in FIG. 17. For example, the physician preferably can select which type of chart is to be used at step 70. If the patient whose eyesight is to be examined is an adult, the physician most likely would select a chart containing test characters such as Snellen letters or numbers. If the patient is a young child, a test character set such as tumbling E's or tumbling C's can be used. The physician can select a predetermined chart or a chart of randomly generated test characters. Charts typically contain a number of lines of test characters of each of a progressively smaller size. If desired, however, the physician can select a chart having only a single line of test characters.

At step 72, the physician can select the desired size of the test characters to be displayed. If the chart that was selected contained a number of lines of test characters, a default range of test character sizes may be provided (e.g., 20/10–20/300). Preferably, the physician can modify the default range at step 72. If the selected chart contains test characters of one size only, then a default size may be provided, which the physician can modify at step 72.

The input interface used by the physician during steps 70 and 72 is preferably either keyboard 22 (FIG. 1) or remote control unit 26. If keyboard 22 is used, then the physician may type in the desired test character sizes, or may select them from a menu on monitor 12. If remote control unit 26 is used, then the various test character sizes are preferably provided on keys 28. Monitor 12 can be used to display an on-screen menu regardless of whether keyboard 22 or remote control unit 26 is used.

After the physician has selected the chart and test character sizes at steps 70 and 72, visual acuity tester 10 displays the chart on the monitor 12 (FIG. 1). This may be done in a number of suitable fashions. One approach is to use a storage-intensive solution, in which large image files are stored for later retrieval when required by visual acuity tester 10. Another approach is to use more computationally-intensive techniques to create the necessary pixel illumination data in real time. In addition, an intermediate approach can be used, in which image files are generated in real-time upon starting-up the computer-based system and stored in, e.g., random-access memory.

With storage-intensive approaches, large data files can be created that contain all of the necessary pixel illumination data to display each test character at each possible size and each possible lane length. Such image data files could contain either the pixel information for entire charts or for individual test characters, which could then be assembled to form the necessary charts. To reduce the amount of data that must be created, the physician can be required to select the lane length from, e.g., a set of 21 discrete lengths ranging from 10 feet to 20 feet in half foot intervals. Further, the image data files can be compressed using any suitable conventional digital image data compression technique.

The available test characters preferably include at least 32 letters, numbers, and special characters (A, B, C, D, E, F, G, H, K, L, N, O, P, R, S, T, V, Z, 2, 3, 4, 5, 6, 7, 8, 9, upward facing "E," left facing "E," downward facing "E," upward facing "C," left facing "C," and downward facing "C"). And there are preferably at least 19 sizes available for the test characters, including: 20/10, 20/15, 20/20, 20/25, 20/30, 20/35, 20/40, 20/50, 20/60, 20/65, 20/70, 20/80, 20/100, 20/125, 20/160, 20/200, 20/250, 20/300, and 20/400. Even if conventional digital image compression techniques were used, the process of storing image data corresponding to each test character at each possible combination of test character size and lane length would involve the storage of very large amounts of image data.

Thus, additional methods preferably are used for handling the data storage task involved in using data image files. One such method involves cross-referencing data image files so that redundant data files can be eliminated. For example, a 20/20 tumbling E at a 20 foot lane length has the same pixel illumination pattern as a 20/15 tumbling E at a 15 foot lane length. It therefore is not necessary to store duplicate data image files for these two situations. Another method for handling large amounts of image data is to use a suitable mass storage medium such as CD-ROM.

A preferred alternative to storing large image files of pixel data is to store the test character data in the form of vector data. Visual acuity tester 10 (FIG. 1) can construct the appropriate pixel data image files from the data records in real time. Generating the image files in real time is more computationally intensive than retrieving stored precalculated image files, but is nevertheless generally preferred, because the storage burden imposed by storing large amounts of pixel data is greatly reduced.

Figure 17:
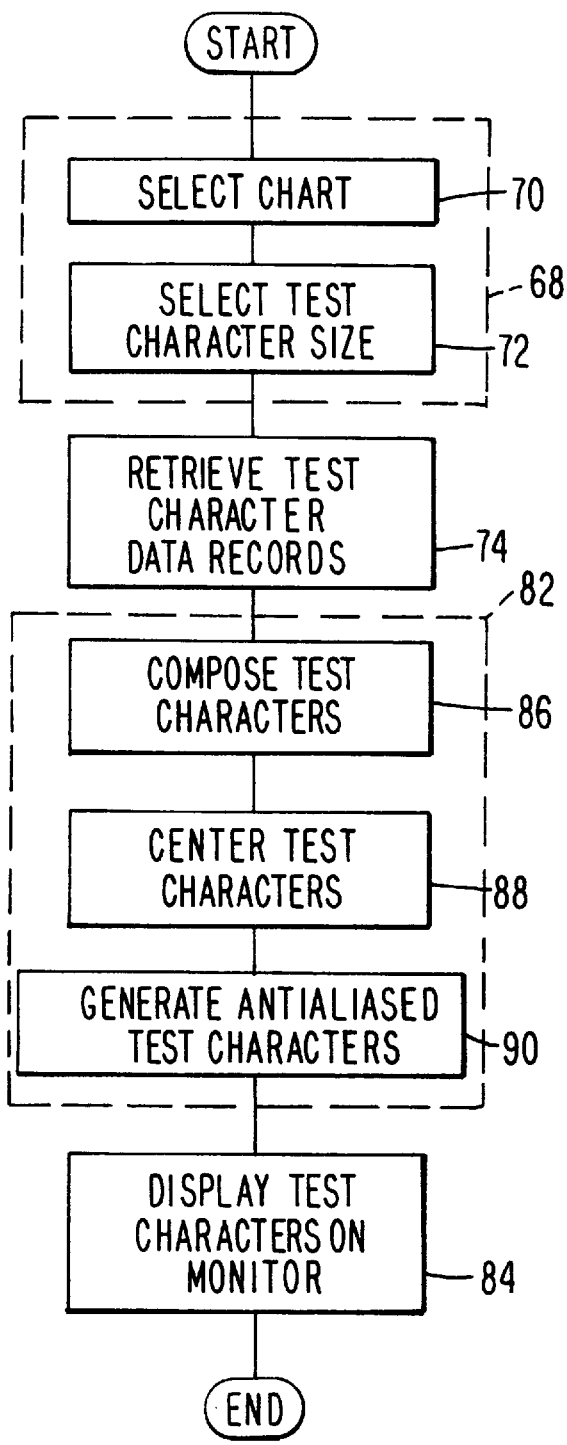
FIG. 17 is a schematic block diagram depicting an illustrative method of displaying a selected set of test characters on a display monitor.

One suitable approach for displaying test characters that avoids the use of large pixel data image files is shown schematically in FIG. 17. At step 74, control unit 16 retrieves test character data records from an appropriate data storage device (FIG. 19), such as an internal hard disk drive. The records contain the data necessary to reconstruct the test character chart that has been selected by the physician. If desired, a separate data record can be provided for each test character, so that only the data records corresponding to test characters that actually appear in a given chart must be retrieved.

One way in which the test characters can be represented in the data records is to divide the lines that define the shape of each character into a number of separate line segments. For example, the data record for the letter "L" could contain six line segments, one for each of the six sides of the L. Each segment can be defined by a set of endpoint coordinates.

Curved line segments can be represented similarly. Preferably, test characters having curved portions may be constructed from elliptical arc segments each having two endpoint coordinates and a center coordinate where one ellipse axis is vertical and the other ellipse axis is horizontal. Curved line segments with a known radius of curvature can also be represented in a data record by beginning and ending coordinates and a radius of curvature. To ensure that such a curved line segment is oriented properly when it is displayed, orientation data (i.e., data that makes it clear in which direction the curved line segment is facing) are also included in the data record.

Figure 18:
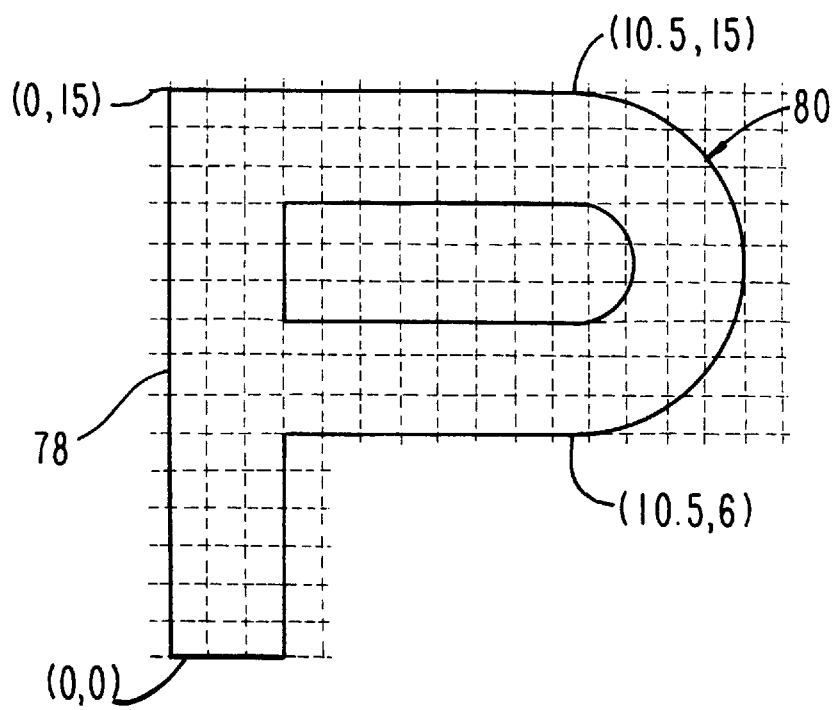
FIG. 18 is a schematic representation of the test character P, showing how the P can be broken into various line segments.

An illustrative test character 13 the letter "P"—is shown in FIG. 18. P 76 can be described by a number of discrete line segments, such as vertical segment 78, which runs from the coordinate (0,0) to coordinate (0,15). Segment 78 can be represented in a data record in a number of suitable formats. For example, both coordinates—(0,0) and (0,15)—may be saved. Alternatively, the initial endpoint (0,0), the direction in which the segment extends (UP), and the length of the segment (15) can be saved. Outer curved segment 80 can be described by the coordinates (10.5,15) and (10.5,6), the radius of curvature (4.5), and the direction in which the segment projects (RIGHT) or can be described by the endpoint coordinates and centerpoint coordinate of an elliptical arc segment.

When storing the various dimensions of the test characters in the test character data records, a standard character size preferably is used. This allows the size of the test characters to be scaled properly during the process of constructing the pixel data for the image from the test character data stored in vector format. For example, all test characters stored in test character data records may have a maximum linear dimension of 15 units. Depending on the selected size of the test character to be displayed, the linear dimensions of the test character can be contracted or expanded.

The process of expanding or contracting the dimensions of the test characters stored in the test character data records is preferably performed during the process of composing the test characters at step 86 of step 82 (FIG. 17). As shown in FIG. 17, at step 82 control unit 16 (FIG. 1) also performs the necessary processing steps to center and antialias the test character information retrieved from the data records at step 74. The resulting test characters are displayed on monitor 12 at step 84.

In performing step 82, control unit 16 (FIG. 1) can use any suitable algorithm for carrying out the processing steps involved in composing, centering, and antialiasing the test characters. For example, control unit 16 composes the test characters that make up the desired chart at step 86, using the endpoint and centerpoint coordinates, length, orientation information etc. retrieved from the data records at step 74. Composing the test characters involves combining the various straight and curved line segments that define the shapes of the test characters to create a complete vector representation of each test character. During the process of composing the test characters, control unit 16 preferably scales the test characters to the desired size. Control unit 16 centers the test characters relative to the pixel array at step 88. At step 90 the characters are antialiased by control unit 16.

Although the steps that make up step 82—composing (step 86), centering (step 88), and generating (step 90)—are shown as separate steps in FIG. 17, these steps, if desired, may be performed simultaneously by control unit 16. For example, control unit 16 can create a centered and antialiased pixel pattern based directly on the test character information stored in the test character data records.

Figure 19:
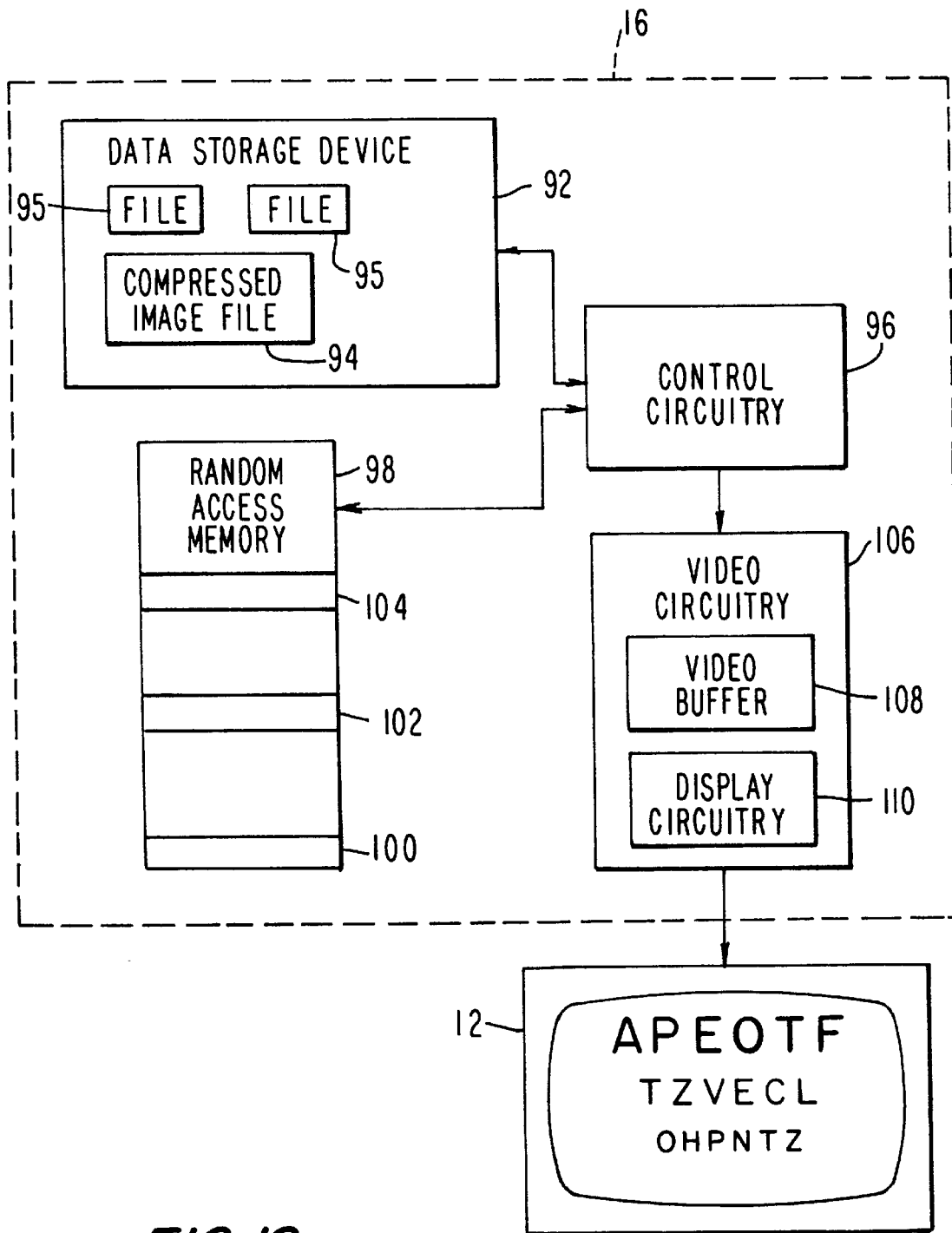
FIG. 19 is a schematic block diagram of the storage and processing scheme used by the control unit of the visual acuity tester to display test characters on the monitor.

The process of displaying the test characters on monitor 12 (FIG. 1) is further illustrated in FIG. 19. As shown in FIG. 19, control unit 16 preferably has a data storage device 92, which may be any suitable storage device, such as a floppy disk drive, a hard disk drive, a tape drive, or an optical disk drive.

The test character data are preferably stored on the data storage device 92 in a suitable data format, such as in the form of a compressed image file 94 or one or more files 95 containing line segment descriptions of the test characters.

Control unit 16 preferably processes the test character data stored in data storage device 92 in real time using control circuitry 96. Because visual acuity tester 10 preferably is based on a conventional personal computer, control unit 16 contains a random access memory 98. Operating system data are loaded into a memory region 100 of random access memory 98. The instructions that control the operation of control circuitry 96 preferably are loaded into a memory region 102. Typically, as control circuitry 96 processes the test character data retrieved from data storage device 92, control circuitry 96 uses a memory region 104 to temporarily store processed test character data.

The type of test character data stored in memory region 104 depends on the data format used to store the test character data in storage device 92, as well as the type of algorithm used to process the data in general. For example, if the test character data in storage device 92 is in the form of files of antialiased and centered pixel information, then the processing function of control circuitry 96 is limited to retrieving the appropriate files and joining together blocks of pixel information to create a selected chart of test characters of a predetermined size. If the test character data in storage device 92 are in a vector format (i.e., if the test characters are stored in the form of line segments) then control circuitry 96 must process the test character data fairly extensively to create the necessary pixel data.

Figure 20:
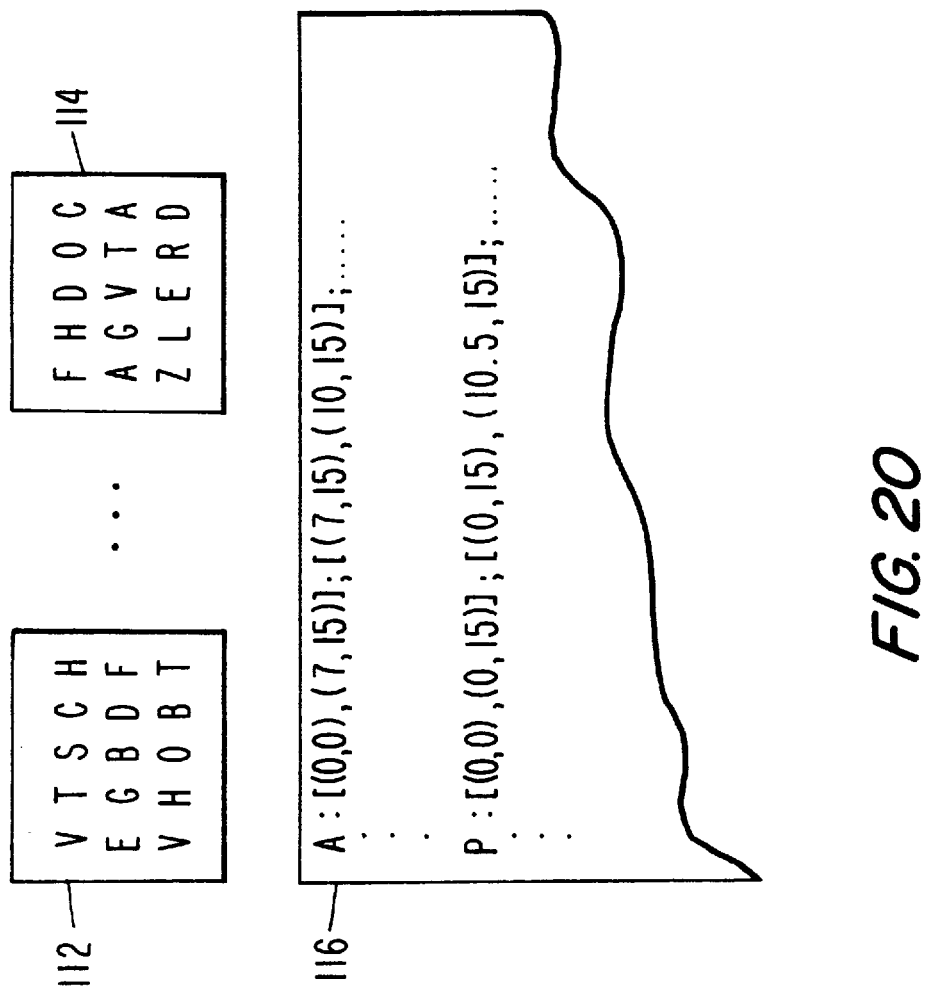
FIG. 20 is a schematic representation of illustrative test character data records showing how test chart data and test character data may be stored in various file structures.

Illustrative test character data records 112, 114, and 116 are shown in FIG. 20. Test character data records 112 and 114 are text files that contain charts that may be selected by a physician. Test character data record 116 contains a vector representation of each of the available test characters. Test characters can also be generated randomly, if desired.

If the physician selects the chart corresponding to test character data record 112, control circuitry 96 processes the test character data in data record 112 using the vector representations in data record 116. Processing test character data records 112 and 116 to transform the vector format into the desired pixel data format requires control circuitry 96 to compose, center, and antialias the test character data in real time. The extent to which the test character data in memory region 104 of FIG. 19 has been processed during each of these steps varies. For example, after the test character data have been retrieved (step 74 in FIG. 17), the data in memory region 104 are in the form of text characters and line segments. Following step 88 of FIG. 17, the data in memory region 104 are in the form of centered pixel information. When step 90 of FIG. 17 has been completed, the data in memory region 104 are typically in the form of centered and antialiased pixel information.

As shown in FIG. 19, control unit 16 preferably contains conventional video circuitry 106, which contains video buffer 108 and display circuitry 110. After the test character data stored in storage device 92 have been processed by the control circuitry 96 to form the desired antialiased and centered pixel information, control circuitry 96 takes the pixel information in memory region 104 and processes it further by placing it into video buffer 108 in the form of pixel data suitable for displaying on monitor 12. Display circuitry 110 uses the pixel data stored in video buffer 108 to generate the image or the test characters on monitor 12.

It will be understood that the foregoing is merely illustrative of the principles of this invention, and that various modifications can be made by those skilled in the art without departing from the scope and spirit of the invention.

What is claimed is:

1. A visual acuity tester for displaying visual acuity test characters of various sizes, comprising:

a storage device for storing test character data for visual acuity testing; wherein:

the test character data are stored in the storage device in the form of test character data records containing line segment data representing the visual acuity test characters; and at least some of the line segment data represent elliptical arc segments;

a control unit;

an input interface coupled to the control unit that allows the control unit to receive physician commands; and a monitor coupled to the control unit; wherein:

the control unit is coupled to the storage device for retrieving and processing the test character data to create antialiased pixel data; and the control unit displays the visual acuity test characters on the monitor by providing the antialiased pixel data to the monitor.

2. The visual acuity tester of claim 1, wherein:

the control unit is responsive to set-up settings; and the set-up settings form part of the physician commands.

3. The visual acuity tester of claim 2, wherein:

the control unit displays the visual acuity test characters on the monitor at sizes appropriate for a predetermined lane length; and the predetermined lane length is one of the set-up settings.

4. The visual acuity tester of claim 2, wherein:

the control unit displays the visual acuity test characters on the monitor at sizes appropriate for a predetermined monitor size; and the predetermined monitor size is one of the set-up settings.

5. The visual acuity tester of claim 2, wherein:

the control unit displays a calibration pattern on the monitor at a predetermined size; and the control unit adjusts the predetermined size of the calibration pattern on the monitor in accordance with at least some of the physician commands.

6. The visual acuity tester of claim 1, wherein the visual acuity test characters on the display form a test chart containing multiple lines of visual acuity test characters having a range of sizes.

7. The visual acuity tester of claim 1, wherein the visual acuity test characters on the display form a test chart containing a single line of visual acuity test characters having a predetermined size.

8. The visual acuity tester of claim 1, wherein each elliptical arc segment is represented by at least a pair of endpoint coordinates and a centerpoint coordinate.

9. The visual acuity tester of claim 1, wherein the character data records further contain text characters.

10. The visual acuity tester of claim 1, wherein the control unit scales the line segment data when the control unit processes the test character data to create the antialiased pixel data.

11. The visual acuity tester of claim 1, wherein at least some of the line segment data are represented by beginning and ending coordinates.

12. The visual acuity tester of claim 1, wherein at least some of the line segment data are represented by a beginning coordinate, a length, and a direction away from the beginning coordinate.

13. The visual acuity tester of claim 1, wherein the test character data stored in the storage device are stored in the form of pixel data image files.

14. The visual acuity tester of claim 1, wherein the antialiased pixel data created by the control unit are unweighted area sampled antialiased pixel data.

15. A visual acuity tester for displaying visual acuity test characters of various sizes, comprising:
   a storage device for storing test character data for visual acuity testing; wherein:
      the test character data are stored in the storage device in the form of test character data records containing line segment data representing the visual acuity test characters; and
      at least some of the line segment data represent elliptical arc segments;
   a control unit;
   an input interface coupled to the control unit that allows the control unit to receive physician commands; and
   a monitor coupled to the control unit; wherein:
      the control unit is coupled to the storage device for retrieving and processing the test character data to create antialiased pixel data;
      the control unit displays the visual acuity test characters on the monitor by providing the antialiased pixel data to the monitor;
      the monitor has a plurality of pixels arranged in a two-dimensional pixel array, each pixel having an associated pixel center and pixel coordinate; and
      the antialiased pixel data provided to the monitor by the control unit contains visual acuity test characters that are centered with respect to the pixel array.

16. The visual acuity tester of claim 15, wherein the antialiased pixel data contain visual acuity test characters that are centered with respect to one of the pixel coordinates.

17. The visual acuity tester of claim 15, wherein the antialiased pixel data contain visual acuity test characters that are centered with respect to one of the pixel centers.

18. The visual acuity tester of claim 15; wherein the antialiased pixel data contain visual acuity test characters that are:
   centered along a first of the two dimensions of the two-dimensional array with respect to one of the pixel coordinates; and
   centered along a second of the two dimensions of the two-dimensional array with respect to one of the pixel centers.

19. A visual acuity tester based on a personal computer for displaying visual acuity test characters of various sizes, comprising:
   a storage device for storing test character data for visual acuity testing; wherein:
      the test character data are stored in the storage device in the form of test character data records containing line segment data representing the visual acuity test characters; and
      at least some of the line segment data represent elliptical arc segments;
   a control unit;
   an input interface coupled to the control unit that allows the control unit to receive physician commands; and
   a monitor coupled to the control unit; wherein:
      the control unit is coupled to the storage device for retrieving and processing the test character data to create antialiased pixel data; and
      the control unit displays the visual acuity test characters on the monitor by providing the antialiased pixel data to the monitor.

20. A method of displaying visual acuity test characters of various sizes with a visual acuity tester based on a personal computer that has a storage device on which test character data are stored, a control unit for processing the test character data, an input interface, and a monitor, the method comprising the steps of:
   receiving physician commands with the control unit via the input interface;
   retrieving the test character data from the storage device with the control unit; wherein:
      the test character data is in the form of test character data records containing line segment data representing the visual acuity test characters; and
      at least some of the line segment data represent elliptical arc segment data;
   processing the test character data with the control unit to create antialiased pixel data; and
      providing the antialiased pixel data to the monitor so that the visual acuity test characters are displayed on the monitor.

21. A visual acuity tester for displaying visual acuity test characters of various sizes, comprising:
   a storage device for storing test character data for visual acuity testing;
   a control unit;
   an input interface coupled to the control unit that allows the control unit to receive physician commands; and
   a monitor coupled to the control unit; wherein:
      the monitor has a plurality of pixels arranged in a two-dimensional pixel array, each pixel having an associated pixel center and pixel coordinate;
      the control unit is coupled to the storage device for retrieving and processing the test character data to create pixel data containing visual acuity test characters that are centered with respect to the pixel array; and
      the control unit displays the visual acuity test characters on the monitor by providing the pixel data to the monitor.

22. The visual acuity tester of claim 21, wherein the pixel data contain visual acuity test characters that are centered with respect to one of the pixel coordinates.

23. The visual acuity tester of claim 21, wherein the pixel data contain visual acuity test characters that are centered with respect to one of the pixel centers.

24. The visual acuity tester of claim 21, wherein the pixel data contain visual acuity test characters that are:
   centered along a first of the two dimensions of the two-dimensional array with respect to one of the pixel coordinates; and
   centered along a second of the two dimensions of the two-dimensional array with respect to one of the pixel centers.

25. The visual acuity tester of claim 21, wherein the test character data are stored in the storage device in the form of test character data records containing line segment data representing the visual acuity test characters.

26. The visual acuity tester of claim 25, wherein at least some of the line segment data represent elliptical arc segments.

27. The visual acuity tester of claim 26, wherein each elliptical arc segment is represented by at least a pair of endpoint coordinates and a centerpoint coordinate.

28. The visual acuity tester of claim 25, wherein the test character data records further contain text characters.

29. The visual acuity tester of claim 25, wherein the control unit scales the line segment data when the control unit processes the test character data to create the pixel data.

30. The visual acuity tester of claim 25, wherein at least some of the line segment data are represented by beginning and ending coordinates.

31. The visual acuity tester of claim 25, wherein at least some of the line segment data are represented by a beginning coordinate, a length, and a direction away from the beginning coordinate.

32. The visual acuity tester of claim 21, wherein the test character data stored in the storage device are stored in the form of pixel data image files.

33. The visual acuity tester of claim 21, wherein the pixel data provided to the monitor by the control unit contain visual acuity test characters that are antialiased.

34. The visual acuity tester of claim 33, wherein the pixel data created by the control unit are unweighted area sampled antialiased pixel data.

35. The visual acuity tester of claim 21, wherein:
the control unit is responsive to set-up settings; and
the set-up settings form part of the physician commands.

36. The visual acuity tester of claim 35, wherein:
the control unit displays the visual acuity test characters on the monitor at sizes appropriate for a predetermined lane length; and
the predetermined lane length is one of the set-up settings.

37. The visual acuity tester of claim 35, wherein:
the control unit displays the visual acuity test characters on the monitor at sizes appropriate for a predetermined monitor size; and
the predetermined monitor size is one of the set-up settings.

38. The visual acuity tester of claim 35, wherein:
the control unit displays a calibration pattern on the monitor at a predetermined size; and
the control unit adjusts the predetermined size of the calibration pattern on the monitor in accordance with at least some of the physician commands.

39. The visual acuity tester of claim 21, wherein the visual acuity test characters on the display form a test chart containing multiple lines of visual acuity test characters having a range of sizes.

40. The visual acuity tester of claim 21, wherein the visual acuity characters on the display form a test chart containing a single line of visual acuity characters having a predetermined size.

41. A method of displaying visual acuity test characters of various sizes with a visual acuity tester that has a storage device on which test character data are stored, a control unit for processing the test character data, an input interface, and a monitor, the method comprising the steps of:
receiving physician commands with the control unit via the input interface;
retrieving the test character data from the storage device with the control unit; wherein:
the test character data is in the form of test character data records containing line segment data representing the visual acuity test characters; and
at least some of the line segment data represent elliptical arc segment data;
processing the test character data with the control unit to create antialiased pixel data; and
providing the antialiased pixel data to the monitor so that the visual acuity test characters are displayed on the monitor.

42. The method of claim 41 further comprising the step of receiving with the control unit a plurality of set-up settings as part of the physician commands.

43. The method of claim 42 further comprising the step of processing the test character data such that the visual acuity test characters are displayed on the monitor at sizes appropriate for a predetermined lane length.

44. The method of claim 42 further comprising the step of processing the test character data such that the visual acuity test characters are displayed on the monitor at sizes appropriate for a predetermined monitor size.

45. The method of claim 42 further comprising the steps of:
displaying a calibration pattern on the monitor at a predetermined size; and
adjusting the predetermined size of the calibration pattern on the monitor in accordance with at least some of the physician commands.

46. The method of claim 41 further comprising the step of providing endpoint coordinates and a centerpoint coordinate as at least some of said arc segment data.

47. The method of claim 41 further comprising the step of providing text characters in the test character data records.

48. The method of claim 41, wherein the step of processing the test character data further comprises the step of scaling the line segment data.

49. The method of claim 41, wherein the step of providing the test character data comprises the step of providing at least some of the line segment data as beginning and ending coordinates.

50. The method of claim 41, wherein the step of providing the test character data comprises the step of providing at least some of the line segment data as a beginning coordinate, a length, and a direction away from the beginning coordinate.

51. The method of claim 41 further comprising the step of storing the test character data in the form of pixel data image files.

52. The method of claim 41 further comprising the step of storing the test character data in the storage device in the form of a test chart containing multiple lines of visual acuity test characters having a range of sizes.

53. The method of claim 41 further comprising the step of storing the test character data in the storage device in the form of a test chart containing a single line of visual acuity test characters having a predetermined size.

54. The method of claim 41, wherein the step of processing the test character data with the control unit comprises the step of processing the test character data with the control unit to create unweighted area sampled antialiased pixel data.

55. A method of displaying visual acuity test characters of various sizes with a visual acuity tester that has a storage device on which test character data are stored, a control unit for processing the test character data, an input interface, and a monitor, the method comprising the steps of:

receiving physician commands with the control unit via the input interface;

retrieving the test character data from the storage device with the control unit; wherein:

the test character data is in the form of test character data records containing line segment data representing the visual acuity test characters; and at least some of the line segment data represent elliptical arc segment data;

processing the test character data with the control unit to create antialiased pixel data; and providing the antialiased pixel data to the monitor so that the visual acuity test characters are displayed on the monitor, wherein the monitor has a plurality of pixels arranged in a two-dimensional pixel array, each pixel having an associated pixel center and pixel coordinate, the method further comprising the step of providing antialiased pixel data to the monitor that contains visual acuity test characters that are centered with respect to the pixel array.

56. The method of claim 55 further comprising the step of providing antialiased pixel data that contain visual acuity test characters that are centered with respect to one of the pixel coordinates.

57. The method of claim 55 further comprising the step of providing antialiased pixel data that contain visual acuity test characters that are centered with respect to one of the pixel centers.

58. The method of claim 55 further comprising the step of providing antialiased pixel data that contain visual acuity test characters that are:

centered along a first of the two dimensions of the two-dimensional array with respect to one of the pixel coordinates; and centered along a second of the two dimensions of the two-dimensional array with respect to one of the pixel centers.

59. A method of displaying visual acuity test characters of various sizes with a visual acuity tester that has a storage device on which test character data are stored, a control unit for processing the test character data, an input interface, and a monitor, wherein the monitor has a plurality of pixels arranged in a two-dimensional pixel array, each pixel having an associated pixel center and pixel coordinate, the method comprising the steps of:

receiving physician commands with the control unit via the input interface;

retrieving the test character data from the storage device with the control unit;

processing the test character data with the control unit to create centered pixel data; and providing the centered pixel data to the monitor so that the visual acuity test characters are displayed on the monitor centered with respect to the pixel array.

60. The method of claim 59 further comprising the step of providing centered pixel data that contain visual acuity test characters that are centered with respect to one of the pixel coordinates.

61. The method of claim 59 further comprising the step of providing centered pixel data that contain visual acuity test characters that are centered with respect to one of the pixel centers.

62. The method of claim 59 further comprising the step of providing centered pixel data that contain visual acuity test characters that are:

centered along a first of the two dimensions of the two-dimensional array with respect to one of the pixel coordinates; and centered along a second of the two dimensions of the two-dimensional array with respect to one of the pixel centers.

63. The method of claim 59 further comprising the step of providing the test character data in the storage device in the form of test character data records containing line segment data representing the visual acuity test characters.

64. The method of claim 63 further comprising the step of providing arc segment data in the test character data records.

65. The method of claim 64 further comprising the step of providing endpoint coordinates and a centerpoint coordinate as at least some of said arc segment data.

66. The method of claim 63 further comprising the step of providing text characters in the test character data records.

67. The method of claim 63, wherein the step of processing the test character data further comprises the step of scaling the line segment data.

68. The method of claim 63, wherein the step of providing the test character data comprises the step of providing at least some of the line segment data as beginning and ending coordinates.

69. The method of claim 63, wherein the step of providing the test character data comprises the step of providing at least some of the line segment data as a beginning coordinate, a length, and a direction away from the beginning coordinate.

70. The method of claim 63 further comprising the step of processing the test character data such that the visual acuity test characters are displayed on the monitor at sizes appropriate for a predetermined lane length.

71. The method of claim 63 further comprising the step of processing the test character data such that the visual acuity test characters are displayed on the monitor at sizes appropriate for a predetermined monitor size.

72. The method of claim 63 further comprising the steps of:

displaying a calibration pattern on the monitor at a predetermined size; and adjusting the predetermined size of the calibration pattern on the monitor in accordance with at least some of the physician commands.

73. The method of claim 59 further comprising the step of storing the test character data in the form of pixel data image files.

74. The method of claim 59 further comprising the step of providing antialiased pixel data to the monitor.

75. The method of claim 59, wherein the step of processing the test character data with the control unit comprises the step of processing the test character data with the control unit to create unweighted area sampled antialiased pixel data.

76. The method of claim 59 further comprising the step of receiving with the control unit a plurality of set-up settings as part of the physician commands.

77. The method of claim 59 further comprising the step of storing the test character data in the storage device in the form of a test chart containing multiple lines of visual acuity test characters having a range of sizes.

78. The method of claim 59 further comprising the step of storing the test character data in the storage device in the form of a test chart containing a single line of visual acuity test characters having a predetermined size.

* * * * *